Figure 1A:
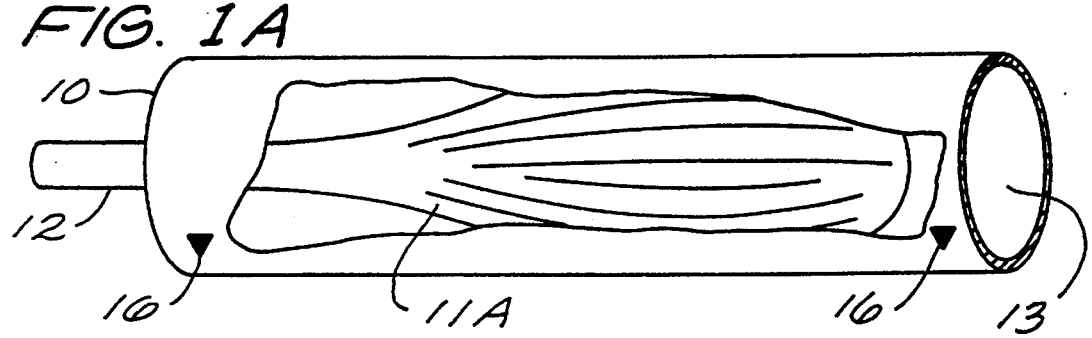

United States Patent

Bircoll

Patent Number: 5,452,732
Date of Patent: Sep. 26, 1995

[54] METHOD OF DISSECTING ALONG CONNECTIVE TISSUE LINES

[76] Inventor: Mel Bircoll, 436 N. Bedford Dr., Ste. 203, Beverly Hills, Calif. 90210

[21] Appl. No.: 233,236

[22] Filed: Apr. 26, 1994

[51] Int. Cl.$^6$ .................................................. A61B 19/00
[52] U.S. Cl. .......................................... 128/898; 606/192
[58] Field of Search .................................. 128/897–898; 623/8, 11; 604/96–99; 606/191–199

[56] References Cited

U.S. PATENT DOCUMENTS

| | | | |
|---|---|---|---|
| 4,624,671 | 11/1986 | Kress | 128/898 |
| 4,685,458 | 8/1987 | Leckrone . | |
| 4,747,405 | 5/1988 | Leckrone . | |
| 4,815,465 | 3/1989 | Alvarado . | |
| 5,022,414 | 6/1991 | Muller . | |
| 5,188,630 | 2/1993 | Christoudias . | |
| 5,195,507 | 3/1993 | Bilweis . | |
| 5,219,355 | 6/1993 | Parodi et al. . | |
| 5,250,060 | 10/1993 | Carbo et al. . | |
| 5,370,134 | 12/1994 | Chin et al. | 128/898 |

OTHER PUBLICATIONS

U.S. Pat. No. 4,841,992, entitled "Tissue Expander" issued to Sasaki on Jun. 27, 1989.
U.S. Pat. No. 4,157,085, entitled "Surgically Implantable Tissue Expanding Device and the Method of its Use" issued to Austad on Jun. 5, 1979.
U.S. Pat. No. 4,955,395, entitled "Tissue Expander and Method of Treating Male Temple Baldness" issued to Manders on Sep. 11, 1990.
U.S. Pat. No. 5,083,576, entitled "Elongation of Linear and Tubular Tissue" issued to Ruiz–Razura et al. on Jan. 28, 1992.
U.S. Pat. No. 5,163,950, entitled "Balloon Catheter and Endoscope Kit" issued to Pinchuk et al. on Nov. 17, 1992.
"Bulbous–Lysing Underminers" by Paul J. Weber, M.D., Alan E. Wulc, M.D., and Leonard M. Dzubow, M.D., dated Dec. 1989, from the J Dermatol Surg Oncol magazine.

Primary Examiner—Lee S. Cohen
Assistant Examiner—John P. Lacyk
Attorney, Agent, or Firm—Ogram & Teplitz

[57] ABSTRACT

An improved dissecting technique in which a balloon dissector having a predetermined inflated size and shape is placed between two naturally occurring layers and then the balloon's envelope is inflated to its full size to force these layers apart. The inflatable balloon is preferably inserted through an incision and is enclosed in a sheath which is removed prior to expansion of the envelope. Once the layers have been so separated, the balloon is deflated and extracted (either by pulling on the fill tube or by reinsertion into the protective sheath). Monitoring of the envelope's positioning is done through either endoscopic monitoring at the surgical site, or using a radiation imaging apparatus (available when the envelope has been treated to be radiopaque). Since the envelope has a predetermined inflated size and shape, the dissection is ideal for such applications as where the entire forehead is to be dissected for a browlift, or to dissect in preparation for breast augmentation.

13 Claims, 4 Drawing Sheets

METHOD OF DISSECTING ALONG CONNECTIVE TISSUE LINES

BACKGROUND OF THE INVENTION

This invention relates to surgical techniques in general and specifically to dissecting along connective tissue line.

Dissection is generally the separation of different structures along natural lines usually by separating the connective tissue framework.

Dissecting surgical tools have been used almost since the dawn of history. These tools are generally divided into blunt dissection and sharp/cutting dissection. As the name implies, sharp/cutting dissection involves the actual cutting of tissue; blunt dissection on the other hand separates along natural lines within the body by breaking the connective tissue.

The breaking of this connective tissue is generally easily accomplished using a variety of tools well known in the surgical field. Examples of tools which utilize a traditional blunt dissection are described in: "Bulbous-Lysin Undermines" by Weber et al. and appearing in *Dermatological Surgery and Oncology*, 15:12, Dec. 1989, page 1252; U.S. Pat. No. 4,815,465, entitled "Dissector Device", issued to Alvarado on Mar. 28, 1989; U.S. Pat. No. 5,188,630, entitled "Christoudias Endopongestick Probe", issued to Christoudias on Feb. 23, 1993; U.S. Pat. No. 5,022,414, entitled "Tissue Separator Method", issued to Muller on Jun. 11, 1991. In all of these devices, a substantially rigid member is pressed against the connective tissue to break them.

In another field of medicine, a "dissection-type" of operation is done in which balloons are used to break plaque build-up in the arterial walls. This operation, named angioplasty, uses a balloon which is inflated in the artery, thereby pressing the plaque against the artery's wall so that the bonding is broken therebetween.

Examples of these devices are shown by U.S. Pat. No. 5,250,060, entitled "Angioplasty Apparatus", issued to Carbo et al. on Oct. 5, 1993; U.S. Pat. No. 4,685,458, entitled "Angioplasty Catheter and Method of Use Thereof", issued to Leckrone on Aug. 11, 1987; U.S. Pat. No. 4,747,405, entitled "Angioplasty Catheter", issued to Leckrone on May 31, 1988; and U.S. Pat. No. 5,219,355, entitled "Balloon Device for Implanting an Aortic Intraluminal Prosthesis for Repairing Aneurysms", issued to Parodi et al. on Jun. 15, 1993. None of these devices though are true dissectors in that they do not break connective tissue but rather only breaking the placque bonding's grip.

Some attempts have been made to use balloons in areas other than in the angioplasty field. One such example is described in U.S. Pat. No. 5,195,507, entitled "Endoscopic Surgical Instrument for Displacing Tissue or Organs", issued to Bilweis on Mar. 23, 1993. As the title implies though, the balloon acts to merely replace or nudge the organ and no actual dissection occurs. Further, for all intents and purposes, the balloon (being made of rubber or an elastic material) is of an indeterminate size and shape, thereby limiting its application to only a few areas.

It is clear that while dissecting remains an integral part of surgery, there hasn't any real development in instruments which are either: tailored for specific applications, or which accomplish the actual dissecting in a gentle and controlled manner.

SUMMARY OF THE INVENTION

The invention is an improved dissecting technique in which a balloon dissector having a predetermined inflated size and shape is placed between two naturally occurring layers and then the balloon's envelope is inflated to its full size to force these layers apart.

The inflatable balloon is preferably inserted through an incision and is enclosed in a sheath which is removed prior to expansion of the envelope. Once the layers have been so separated, the balloon is deflated and extracted (either by pulling on the fill tube or by reinsertion into the protective sheath).

Monitoring of the envelope's positioning is done through either endoscopic monitoring at the surgical site, or using a radiation imaging apparatus (available when the envelope has been treated to be radiopaque). Since the envelope has a predetermined inflated size and shape, the dissection is ideal for such applications as where the entire forehead is to be dissected for a browlift, or to dissect in preparation for breast augmentation.

The invention uses a balloon dissector for use in surgery in which the balloon is constructed of a substantially non-elastic material (such as a polyester film) so that its volume and shape are predetermined at the time of manufacture. With the ability to control the shape during manufacture, the dissector is developed for specific applications within the patient so as to follow naturally occurring lines within the body. As such, the dissector is especially useful for such applications as the forehead dissection (browlifts) and breast dissection (breast augmentation).

Dissection by the balloon is either through a blunt dissection or a sharp dissection using selective manufacture of the balloons edges. Edges, usually formed at the intersection of two sheets of material, can be either blunt (folded inward) or sharp (folded outward and hardened). In this manner, the balloon dissector is specifically designed for certain applications.

One embodiment of the invention is made radiopaque so that its inflation's progress is monitorable using existing radiation imaging devices.

The balloon dissectors of this invention are a new type of surgical instrument that utilizes volume expansion to create surgical planes and dissection spaces in a variety of surgical procedures. In application, the instrument is placed into the proper surgical plane through a small incision.

In the preferred embodiment of the invention, proper placement of the dissector is ascertained by endoscopic evaluation. In another embodiment, the balloon is constructed of a radiopaque material so that its placement is ascertainable using radiation imaging devices well known to those of ordinary skill of the art.

The device is expanded by filling its volume with either: air (balloon pneumatic dissector), or fluid, i.e. water or saline (balloon fluid dissectors). The balloon or expandable envelope is manufactured of a substantially non-elastic material such as a polyester film material commercially available from Du Pont Corporation and known under the trademark "Mylar".

Because the balloon has a fixed shape and volume, the surgeon is able to use the tool in a variety of circumstances where control is required. The expandable envelope is simply inflated to its capacity to obtain the desired dissection shape and extent.

As such, the instrument is a new surgical tool and is considered a primary tool and a basic surgical instrument in support of expansion dissection. This type of dissection affects at once plane creation and tissue expansion, both of which are needed in the performance of multiple surgical procedures.

These balloon dissectors are made in various sizes and with different shapes depending on the space the surgeon is attempting to create. For example, the invention is made in round, square, rectangular and oblong shapes. For use in the breast the apparatus is designed with flat posterior surface and a convex anterior surface. Another variation for the scalp has a mild concave inferior surface with a convex superior surface. The invention includes all shapes and configurations.

The dissector of this invention is preferably made of a heat sealed, rigid balloon material such as Mylar. Use of another, or similar material is also be acceptable. The balloon preferably has reinforced ribbing to allow its compression to a small cylinder so that the balloon will fit into a sheath.

The sheath, in the preferred embodiment, is an integral part of the assemblage. With the balloon protected by the insertion sheath, it is placed in proper position within the patient. Once the dissector is in place, the sheath is withdrawn, thereby exposing the balloon for use. On other embodiments of this invention, the sheath remains attached for further use in the operation.

A fill tube is used to inflate the balloon dissector. The fill tube portion is strongly reinforced into the "body" of the balloon. Fill tubes are of varying length. The fill tube serves two functions:

1. The expandable envelope is filled with air or liquid using the fill tube (The fill tube ends in a "lure-lock" device so that it may be attached to a syringe or mechanized pump for filling); and,
2. At the completion of expansion and surgical space creation, the balloon is removed by pulling on the fill tube (an alternative embodiment removes the balloon by placing it again into the sheath).

In the preferred embodiment, the apparatus is a single use device and is disposable. Preferably, the devices are sold in "kits" which contain multiple sizes of dissectors. The "kits" are intended to be classified in accordance with types of procedures.

Applications for this invention are numerous including:

1. Endoscopic Mammaplasty (i.e., placing a mammary saline prosthesis through a minimal incision);
2. Endoscopic Face Lift (the configuration of the DISSECTOR is specifically designed to fit the contours of the face);
3. Scalp reduction (i.e. the removal of bald portions of the scalp); Using this apparatus, advancement flap closures are easily performed. This involves placement of a balloon dissector, the bloodless expansion of the tissue, excision of the lesion and the closure in layers.

This new technique is for use in the excision and defect repair of:
   a. Cancers;
   b. Moles and other benign lesions;
   c. Congenital lesions such as but not limited to:
      1. birth marks;
      2. port wine stains;
      3. hemangiomas;
   d. Inflammatory lesions;
   e. Any surgical condition that is characterized by a skin deficiency before or after excision;
   f. Traumatic injuries of the skin;
   g. Any surgical condition in which there is the desire to create a surgical plane or space.

This apparatus is a primary surgical tool and is used with other existing surgical tools.

The ability to expand skin and use this new conceptual technique and instrumentation is dependent on the unique qualities of the skin. The quality of skin depends predominantly on the twin networks of protean collagen and elastin and their interwoven architecture. As load increases on the skin, random arrangements of these fibers come more into alignment in the direction of the stretching force.

The skin possesses viscoelastic properties of creep and stress relaxation. Creep relates to stretch of the skin when force is kept constant. Stress relaxation relates to the condition in which a stretched distance for skin is maintained while the force needed to maintain stretch is gradually decreased.

The viscoelastic properties are relied upon to effect skin expansion and are called into play with the use of this new dissection concept. They are known and scientifically proven properties of skin.

The invention, together with various embodiments thereof will be more fully described by the accompanying drawings and the following descriptions.

DRAWINGS IN BRIEF

FIGS. 1A, 1B, 1C, 1D, and 1E show various embodiments of the invention's expandable envelope or balloon.

FIGS. 2A, 2B, 2C, and 2D illustrate the application of the invention's balloon and the dissecting action caused by its inflation.

Figure 3A:
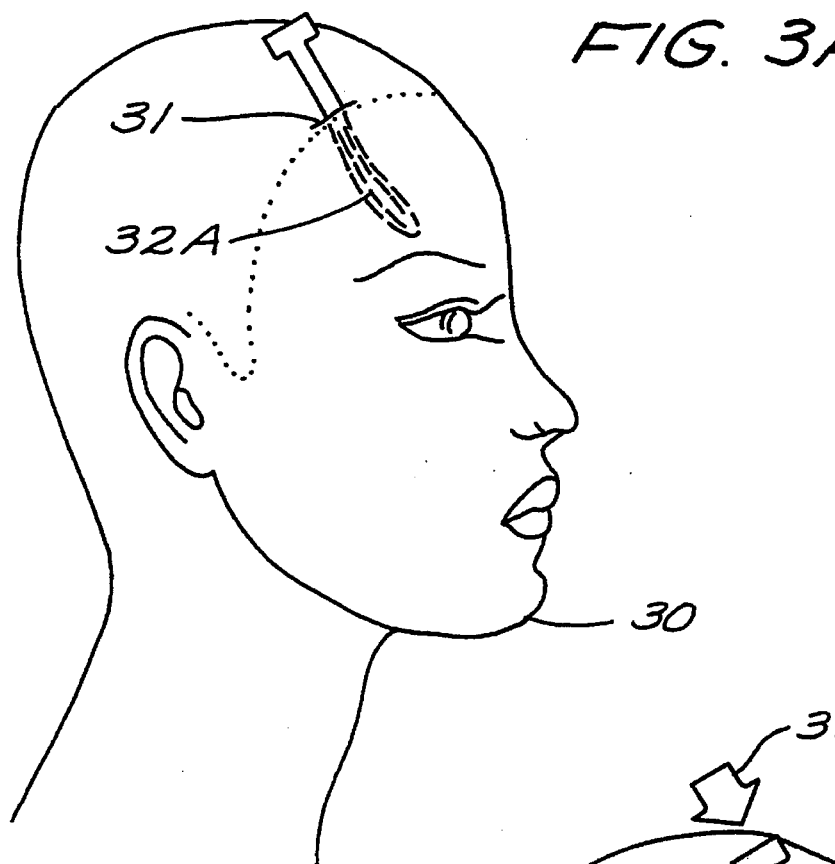
Figure 3B:
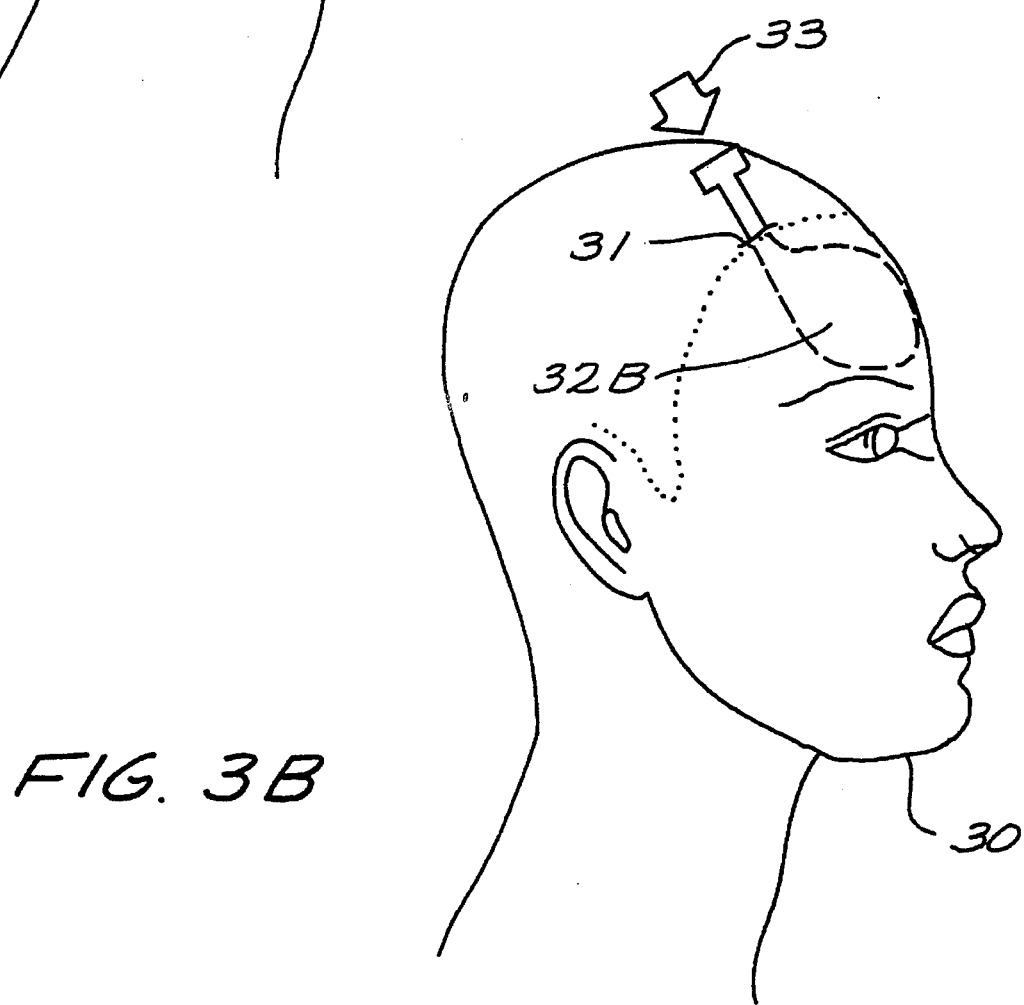

FIGS. 3A and 3B illustrate an embodiment of the invention in which a balloon dissector is used in preparation for a brow-lift.

Figure 4:
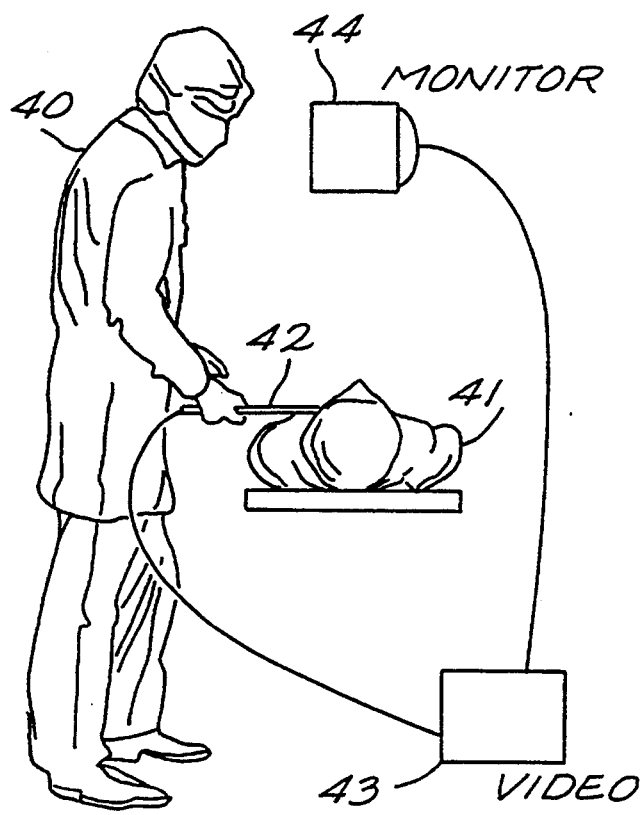

FIG. 4 diagrams the use of the invention in conjunction with an endoscope.

Figure 5:
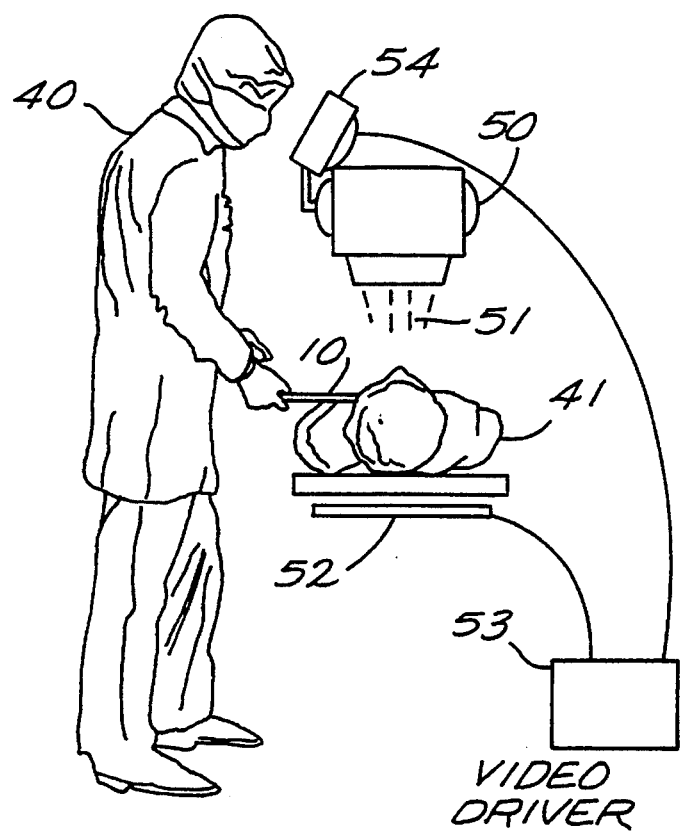

FIG. 5 diagrams the use of the invention in conjunction with a radiation imaging apparatus.

DRAWINGS IN DETAIL

FIGS. 1A, 1B, 1C, 1D, and 1E show various embodiments of the invention's expandable envelope or balloon.

FIG. 1A illustrates an embodiment of the invention in which a sheath 10 is used to surround and protect the expandable envelope 11A. Sheath 10 provides a good mechanism for the insertion and positioning of the invention at the proper locale within the invention.

During the positioning of sheath 10, the surgeon (not shown) uses indicia 16 for the proper orientation of sheath 10 so that when the expandable envelope 11A is extracted from sheath 10, via opening 13, the expandable envelope 11A is properly oriented for the task at hand. In this illustration, indicia 16, being triangles, are to be positioned next to the bone.

Once sheath 10 is properly inserted and positioned, the expandable envelope 11A is removed from sheath 10 by pulling sheath 10 away leaving expandable envelope 11A in place. The expandable envelope 11A is then inflated via fill tube 12 to accomplish the desired dissection.

Inflation of the expandable envelope 11A is accomplished through a variety of methods well known to those of ordinary skill in the art including, but not limited to, the introduction of a medium such as sterile saline water, or a gas medium.

The expandable envelope 11A is constructed of substantially non-elastic material so that it will take on a predetermined and well defined shape and contour.

After the dissection has been accomplished, the expandable envelope 11A is deflated and extracted from the body. Extraction is through a variety of ways and, in one embodiment, involves the re-insertion of expandable envelope 11A into sheath 10 for removal. Another extraction technique is pulling on the fill tube to withdraw the deflated expandable envelope through the entry incision.

Figure 1B:
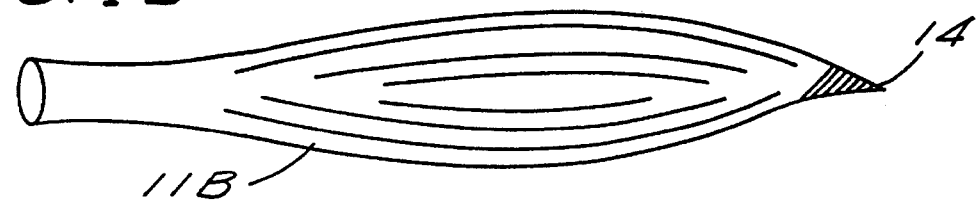

FIG. 1B illustrates an embodiment of the invention in which a sharp dissector 14 is included on expandable envelope 11B. Manufacture of the sharp dissector is accomplished through a variety of techniques well known to those of ordinary skill in the art. In the preferred embodiment, naturally occurring seams in the material constructing the expandable envelope 11B are turned outward and then are harden to provide a stiff cutting edge.

Figure 1C:
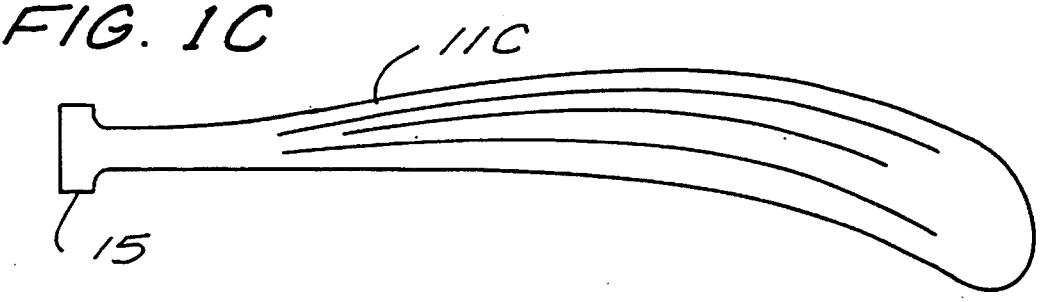

FIG. 1C illustrates another embodiment of the invention in which the expandable envelope is shaped in a curving manner. Expandable envelope 11C is filled using luer lock 15 permitting a standard syringe to be used for inflation of the envelope 11C.

This embodiment, 11C, has only blunt sides and therefore is used for blunt dissection whereas the embodiment of FIG. 1B is used for sharp dissection.

The curved shape of expandable envelope 11C is conducive where the dissection is to follow a naturally occurring line within the body that curves. This shaped dissector dissects only the area of interest and causes little ancillary damage.

Figure 1D:
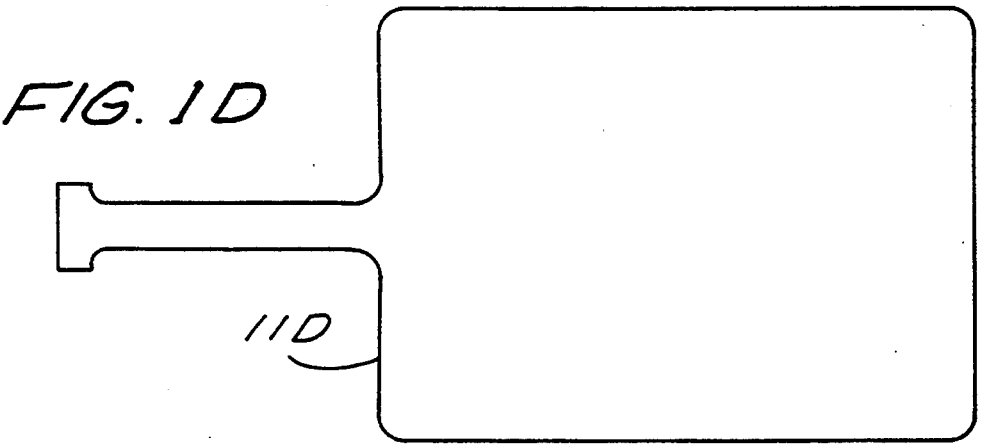
Figure 1E:
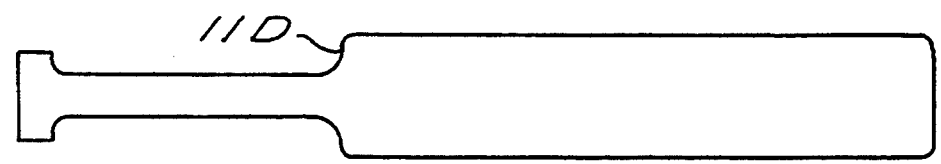

FIGS. 1D and 1E illustrate a top and side view respectively of a rectangular shaped expandable envelope 11D. The rectangular shape is beneficial for a number of applications and is used where a relatively large area is to be dissected.

FIGS. 2A, 2B, 2C, and 2D illustrate the application of the invention's balloon and the dissecting action caused by its inflation.

Body parts 20A and 20B are connected by connective tissue 21A. Through traditional techniques, sheath 10, containing an expandable envelope, is inserted into this connective tissue leaving fill tube 12 exposed for use by the surgeon.

Figure 2A:
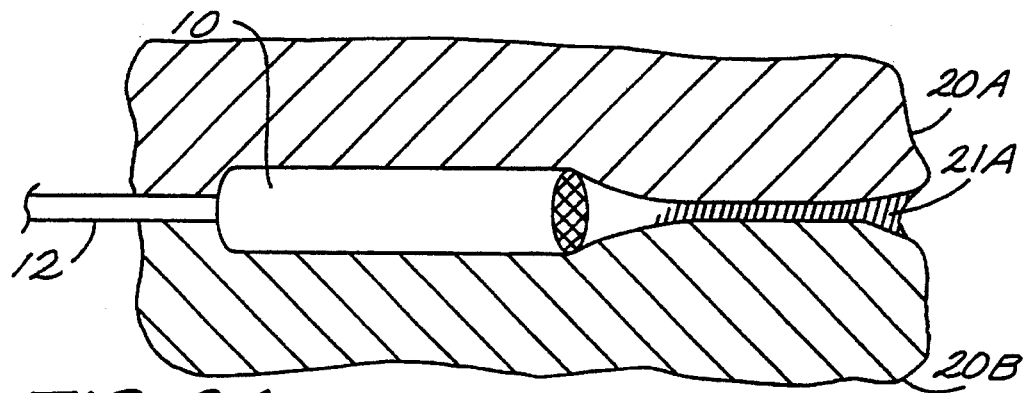
Figure 2B:
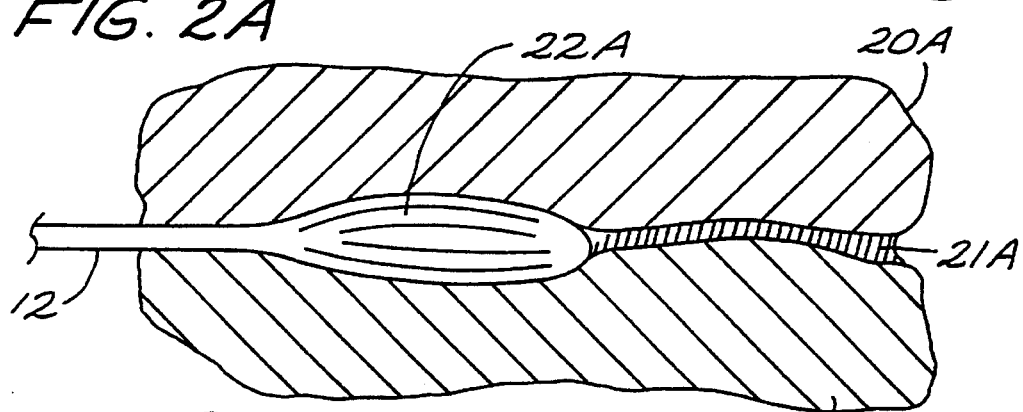
Figure 2C:
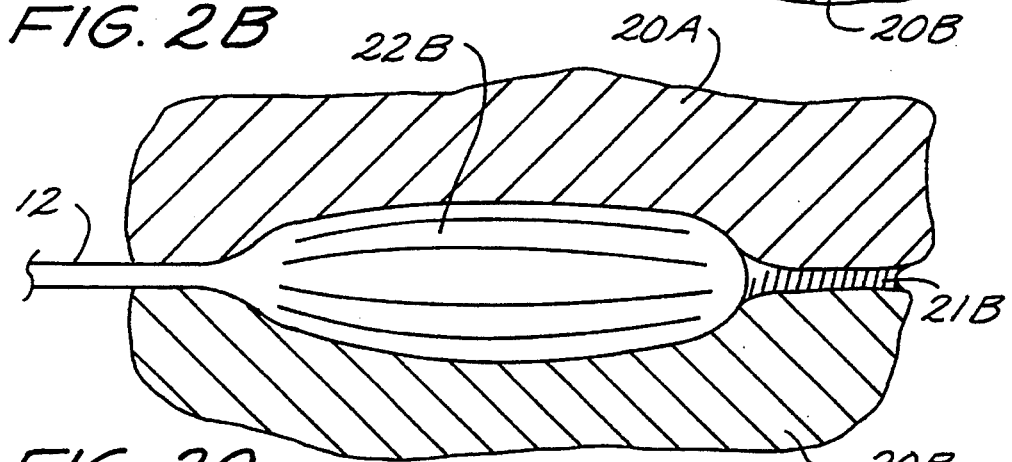

The sheath is removed, FIG. 2B, leaving the deflated expandable envelope 22A behind.

Figure 2D:
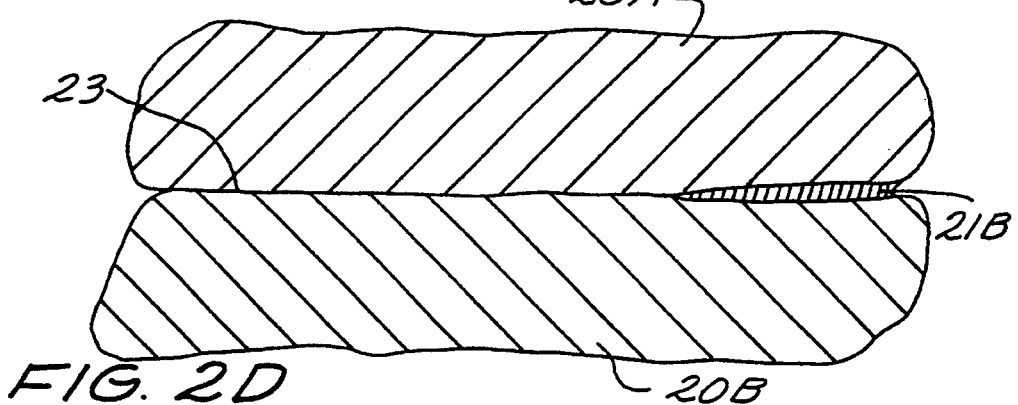

Using fill tube 12, a medium is inserted into the expandable envelope 22B whereupon envelope 22B expands to its fully size and shape, thereby dissecting along the connective tissue layer 21B, FIG. 2D.

Once full dissection has occurred, the expandable envelope 22B is deflated and removed from the surgical site, leaving the intersection 23 between body parts 20A and 20B without any connective tissue, FIG. 2D. At this point, the surgeon is free to use this dissected area for whatever purpose is desired.

Body parts 20A and 20B can be any parts of the body including: skin, organs, muscle, bone, etc.

FIGS. 3A and 3B illustrate an embodiment of the invention in which a balloon dissector is used in preparation for a brow-lift.

Patient 30 has a small incision 31 made in or near the hair-line. Incision 31 permits the introduction of expandable envelope 32A into a desired location between the bone and overlying tissue.

As the expandable envelope is inflated 32B, through the introduction of medium 33, FIG. 3B, dissection is made between the bone and overlying tissue. For a brow-lift operation then, full dissection has been accomplished without excessive trauma to the patient.

FIG. 4 diagrams the use of the invention in conjunction with an endoscope.

Endoscopes are generally fiber-optic cameras which are inserted into a patient through a small incision opening. These cameras give the surgeon a view of area immediately in front of the lens.

In certain instances, positioning of the dissector of this invention is critical and is accomplished using a conventional endoscope well known to those of ordinary skill in the art.

Surgeon 40 manipulates endoscope 42 to a site near the position of the balloon dissector (positioned behind the endoscope 42 in this illustration). Endoscope 42 captures the image and communicates it to the video electronics 43 which creates a video image viewable by surgeon via monitor 44.

In this context then, the dissecting steps of the present invention become:
 a) creating an incision in the patient;
 b) inserting, via said incision, a sheath having enclosed therein the expandable envelope of this invention;
 c) positioning said sheath within said patient at a selected surgical site by (when an endoscope is used):
  1) creating a second incision in the patient;
  2) inserting the endoscope into the patient via said second incision;
  3) positioning a viewing end of said endoscope near said selected surgical site; and,
  4) monitoring the sheath's position via said endoscope.
 d) withdrawing said sheath to expose said expandable envelope; and,
 e) expanding said expandable envelope by communicating a medium via a fill tube communicating with said expandable envelope.

Once the dissection has been accomplished, the steps for removal of the balloon dissector are:
 a) collapsing the expandable envelope by removing the medium; and,
 b) removing said expandable envelope from the patient by either pulling it through the first incision using the fill tube, or by re-inserting the envelope into the sheath and then removing the sheath.

In this manner, the proper positioning of the expandable envelope is accomplished with extreme precision.

FIG. 5 diagrams the use of the invention in conjunction with a radiation imaging apparatus.

When radiation imaging is to be used, the preferred embodiment of the expandable envelope is radiopaque so that it can be seen and distinguished among the body's tissue. Making the expandable envelope radiopaque is easily accomplished by either coating the insides of the envelope with a radiation opaque metal during its manufacture; or, by introducing barium or another metal during the inflation of the envelope. Those of ordinary skill in the art readily recognize other techniques which will accomplish this objective.

In the case where radiation imaging is used, radiation from source 50 is directed, 51, towards patient 41 and passes therethrough to impinge upon sensor plate 42 which translates the image into an electronic representation. This electronic representation is communicated to video driver 53 which creates an image via monitor 54.

This image from monitor 54 assists surgeon 40 in the positioning of the sheath 10 within the patient. Once the sheath has been removed and the expandable envelope is being inflated, its progress is easily monitored using the image from monitor 54.

In this manner, the insertion and inflation of the expandable envelope is monitored throughout the process.

It is clear from the foregoing that the present invention creates an improved apparatus and method for dissecting.

What is claimed is:

1. A method for surgically dissecting comprising the steps of:
   a) creating an incision in a patient;
   b) inserting, via said incision, a sheath having enclosed therein an expandable envelope having a predefined shape and volume, said envelope constructed of a non-elastic material and being removable from said sheath;
   c) positioning said sheath within said patient at a selected surgical site between tissue of said patient;
   d) adjusting said sheath's orientation in said patient based upon an indicia located on said sheath;
   e) withdrawing said sheath to expose said expandable envelope; and,
   f) dissecting the tissue by expanding said expandable envelope by communicating a medium via a fill tube communicating with said expandable envelope.

2. The method for surgically dissecting according to claim 1 wherein the step of positioning said sheath includes the steps of:
   a) creating a second incision in said patient;
   b) inserting an endoscope into said patient via said second incision;
   c) positioning a viewing end of said endoscope near said selected surgical site; and,
   d) monitoring said sheath's position via said endoscope.

3. The method of surgically dissecting according to claim 2 wherein the step of positioning said sheath includes the step of placing said sheath between two naturally occurring layers of said patient's body.

4. The method for surgically dissecting according to claim 1 wherein the step of positioning includes the step of creating an image of said expandable envelope using radiation imaging techniques.

5. The method of surgically dissecting according to claim 1 further including the steps of:
   a) collapsing said expandable envelope by removing said medium from said expandable envelope; and,
   b) removing said expandable envelope from the patient.

6. The method of surgically dissecting according to claim 5 wherein the step of removing said expandable envelope includes the step of re-inserting said expandable envelope in said sheath.

7. The method of surgically dissecting according to claim 6 wherein the step of removing said expandable envelope includes the step of withdrawing said expandable envelope by pulling on said fill tube.

8. A method for dissecting along connective tissue comprising the steps of:
   a) creating an incision in a patient;
   b) inserting, via said incision, a sheath having enclosed therein an expandable envelope having a predefined shape and volume, said expandable envelope constructed of a non-elastic material and being removable from said sheath;
   c) simultaneously,
      1) visualizing said sheath within the patient's body, and,
      2) positioning said sheath within said patient at a selected surgical site based upon an indicia located on said sheath such that said sheath lies between naturally occurring layers of the patient's body;
   d) withdrawing said sheath to expose said expandable envelope; and,
   e) expanding said expandable envelope by communicating a medium via a fill tube communicating with said expandable envelope.

9. The method for dissecting according to claim 8 further including the steps of:
   a) creating a second incision in said patient;
   b) inserting an endoscope into said patient via said second incision;
   c) positioning a viewing end of said endoscope near said selected surgical site; and, wherein the step of visualizing said sheath includes the step of monitoring said sheath's position via said endoscope.

10. The method for dissecting according to claim 8 wherein the step of visualizing said sheath includes the step of creating an image of said expandable envelope in said patient using a radiation imaging apparatus.

11. The method of dissecting according to claim 8 further including the steps of:
    a) collapsing said expandable envelope by removing said medium from said expandable envelope; and,
    b) removing said expandable envelope from the patient.

12. The method of dissecting according to claim 11 wherein the step of removing said expandable envelope includes the step of re-inserting said expandable envelope in said sheath.

13. The method of dissecting according to claim 11 wherein the step of removing said expandable envelope includes the step of withdrawing said expandable envelope by pulling on said fill tube.

* * * * *